United States Patent
Reynaud et al.

[11] Patent Number: 5,989,032
[45] Date of Patent: Nov. 23, 1999

[54] SELF-LOCKING DENTAL REINFORCEMENT

[75] Inventors: Marc Reynaud, Meylan; Pierre-Luc Reynaud; Manh Chu, both of Saint-Egreve, all of France

[73] Assignee: Societe de Recherches Techniques Dentaires R.T.D., Saint-Egreve, France

[21] Appl. No.: 08/894,002

[22] PCT Filed: Feb. 16, 1996

[86] PCT No.: PCT/FR96/00254

§ 371 Date: Aug. 11, 1997

§ 102(e) Date: Aug. 11, 1997

[87] PCT Pub. No.: WO96/25119

PCT Pub. Date: Aug. 22, 1996

[30] Foreign Application Priority Data

Feb. 17, 1995 [FR] France .................................. 95 01870

[51] Int. Cl.$^6$ .......................................... A61C 5/04
[52] U.S. Cl. .......................................... 433/224; 433/220
[58] Field of Search .................................. 433/220, 221, 433/225, 226, 224

[56] References Cited

U.S. PATENT DOCUMENTS

| | | |
|---|---|---|
| 1,397,067 | 11/1921 | Williams . |
| 4,696,646 | 9/1987 | Maitland . |
| 5,007,837 | 4/1991 | Werly ........................................ 433/226 |
| 5,073,112 | 12/1991 | Weil ........................................ 433/224 |
| 5,074,792 | 12/1991 | Bernadat .................................. 433/220 |
| 5,284,443 | 2/1994 | Weil ........................................ 433/224 |
| 5,326,263 | 7/1994 | Weissman ................................ 433/225 |
| 5,547,379 | 8/1996 | Hasel ..................................... 433/212.1 |
| 5,803,736 | 9/1998 | Merritt, Jr. .............................. 433/213 |

FOREIGN PATENT DOCUMENTS

| | | |
|---|---|---|
| 2 493 698 | 5/1982 | France . |
| 2 669 211 | 5/1992 | France . |
| 38 25 601 | 3/1989 | Germany . |
| WO93/25158 | 12/1993 | WIPO ................................... 433/224 |

*Primary Examiner*—Ralph A. Lewis
*Attorney, Agent, or Firm*—Young & Thompson

[57] ABSTRACT

Dental post to be fitted, particularly, within a dental cavity (3) comprises axial and longitudinal stiffening elements (7). At least a portion of the stiffening elements which is to be fixed within the cavity (3) comprises, at least at its periphery, a curable product (9) capable of yielding under an applied force so as to conform to the walls of the cavity in which it is located. The product is curable after being introduced into the cavity.

11 Claims, 2 Drawing Sheets

SELF-LOCKING DENTAL REINFORCEMENT

FIELD OF THE INVENTION

The present invention relates to a dental reinforcement, in particular a post, whose outer shape is able to fit the contour of a cavity, or of the root canal, of a tooth to which it is to be fixed.

BACKGROUND OF THE INVENTION

In odontology posts are known to be used in metal or a composite material to reconstruct a root treated tooth.

These posts, of whatever material they are made, have a circular cross-section which means that when they are placed in dental root canals whose cross-section is of a different shape, only a small part of their outer surface comes into contact with the inner wall of the tooth. Mechanical locking of the post is therefore not fully effective, and it is sometimes necessary to improve the lock by inserting various reconstruction or cementing products into the free spaces between the tooth and the post.

If the practitioner wishes to achieve a perfect fit of the post inside an ovoid root canal, a very precise root canal impression has to be made for example in silicon which is forwarded to a prosthesis laboratory to have a so-called anatoform post made of cast metal, which has the disadvantage of being costly and requires three successive procedures which can be a source of imprecision, these being taking an impression of high accuracy, making a wax post in this impression and finally casting the metal post with the risk of over-sizing at the time of casting.

Patent FR-A-2 669 211 proposed filling the spaces between the post and the root canal with an injection of setting resin which also bonds the post to the canal. One disadvantage of this technique is that the extent of shrinkage which takes place in the resin during setting increases with the mass of resin. Under these conditions the shrinkage which occurs in different places within the root canal can be extensive and creates areas in which bonding is not satisfactory.

Document DE-A-3 825 601 also describes a dental post whose upper end is provided with a part of truncated cone shape forming a core of greater diameter intended to reconstruct a deteriorated tooth. This dental post is positioned in the root canal of the tooth and is made up of a synthetic product containing fibres which may be carbon or glass fibres. This type of post is fixed in the root canal of the tooth by bonding or cementing means. Such device has drawbacks similar to those described in the document mentioned previously.

The purpose of the present invention is to remedy such drawbacks. This invention therefore sets out to improve both the ease and quality of applying reinforcements to a dental cavity. One particular purpose of the present invention is to propose a dental reinforcement which is able to fit the contour of the cavity, or root canal, in which it is to be positioned.

SUMMARY OF THE INVENTION

The aim of the present invention is therefore a dental reinforcement intended to be placed in particular in a dental cavity, characterized in that it comprises means of longitudinal rigidity of which at least the part intended to be fixed inside said cavity comprises, at least on its periphery, a setting product able to flow under stress so that it follows the contour of the walls of the cavity in which it is placed, said product being able to set after it has been placed in said cavity.

In accordance with the invention, the reinforcement may in particular be a post, or a core which can be fitted to a post bonded to a tooth. The reinforcement may also be made up of a single part which constitutes both the post and the core.

In one embodiment of the invention, the means of longitudinal rigidity are made up of a rigid nucleus formed in particular of long fibres embedded in a synthetic resin. Such fibers may, preferably, be transparent and particular use is made of glass or quartz fibres or optic fibres.

Under another embodiment of the invention said reinforcement is of a type which sets by polymerization under the action of a light ray. This embodiment is of particular interest as it provides the practitioner with all the time that is needed to position the reinforcement in the patient's tooth and allow the setting product to flow during said positioning into the dental cavity it is intended to fill.

According to the invention, the product may also be of a type which sets by chemical reaction or under the effect of high frequency or micro-wave radiation.

A further purpose of this invention is a method of inserting a dental reinforcement in a dental cavity, characterized in that it comprises the following stages:

covering, at least around its periphery, a longitudinal rigid element with a setting product able to flow under stress, placing said reinforcement made in this way inside the cavity in such manner as to allow said product to flow under the stress resulting from the application of the reinforcement inside the cavity so that it follows the contour of the walls of the cavity in which it is placed, causing said product to set at least in part, withdrawing said reinforcement from the cavity, placing a cementing product in said cavity and/or along the periphery of said reinforcement, re-placing the reinforcement inside the cavity so that it is cemented into place.

With this method it is possible to finish the setting of said product covering the element of longitudinal rigidity of the reinforcement, outside the tooth cavity, and in particular in an oven, which allows the setting operation to be closely controlled so that the reinforcement can be given strong rigid properties.

BRIEF DESCRIPTION OF THE DRAWINGS

A form of embodiment is described below for illustration purposes which is non-restrictive and refers to the appended drawing in which.

DESCRIPTION OF THE PREFERRED EMBODIMENT

Figure 1:
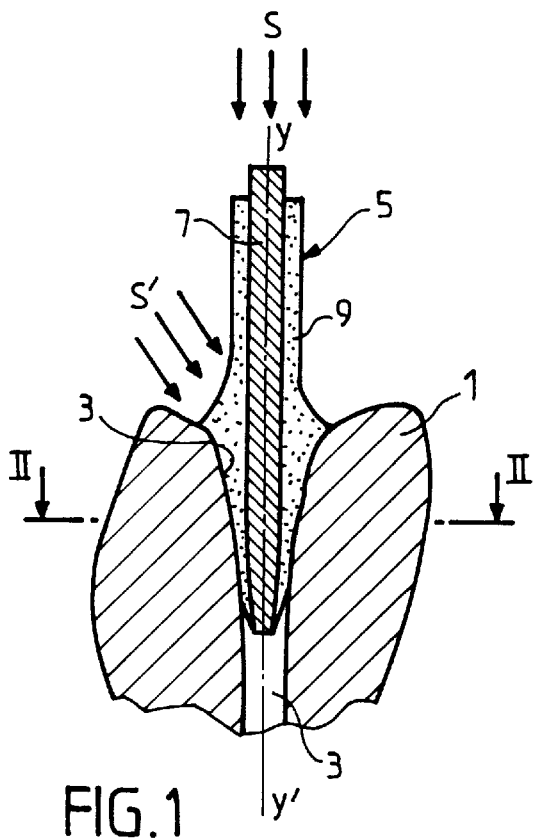
FIG. 1 is an axial, longitudinal section view of a reinforcement of the invention made up of a post placed in a root canal.

FIG. 1 shows a tooth 1, comprising an ovoid canal 3 whose upper part has been enlarged so that it can house a post 5 of the invention.

Post 5 is made up of a central, longitudinal nucleus with an axis yy' which is transparent and made up of a bundle of long fibers, such as quartz or glass fibers, which are embedded in a setting resin matrix, in particular a transparent resin such as an epoxy resin.

The periphery of nucleus 7 is covered by a malleable product 9 having the property of adhering to nucleus 7 and of setting under the action of a light ray, in particular a ray whose wavelength is such that it is located in visible light. Products of this type are fully known in dental art and particular use may be made of a triethylene glycol dimethacrylate resin (so-called TGDMA) or a bisphenol aglycidyl dimethacrylate resin (so-called BISGMA).

Characteristics are given to setting product 9 such that it may be deformed and flow easily when it is subjected to stress, so that, when post 5 is positioned in canal 3, it is able to fill the empty volume surrounding it.

In order to give the setting product the required compactness, microloads may be added to it, in particular pyrogenated or colloidal silica which will give it thixotropic characteristics.

Also said setting product may be loaded, in addition to silica loads, with loads such as short fibers placed in random position and direction in said product, or long fibers wound for example around axial and longitudinal means of rigidity. Depending upon specific applications, macroloads may also be added to the product made up in particular of quartz particles or hollow glass microspheres. Preferably, according to the invention, the loads placed in the setting product are made up transparent materials. According to the invention, the loads whether made up of silica or fibers, are used to provide control over the fluid, malleable nature of the product which will determine its flow capacity when the post is set in place. In the present example, the product is a setting product which is set by photopolymerization.

Under these conditions the invention is put to use as described below.

Figure 2:
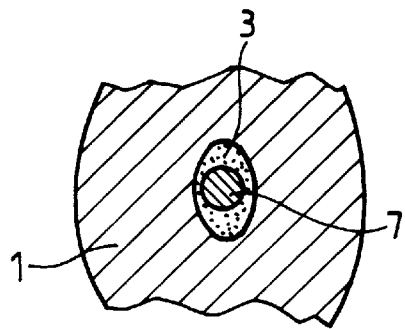
FIG. 2 is a transverse section view of the post represented in FIG. 1 along line II—II of the latter.

When the practitioner has finished the canal preparation of root canal 3 after acid etch and drying, an adhesive "Primer" and an adhesive is applied to the outer wall of post 5 and to the walls of the canal. Post 5 is then placed in root canal 3. Under the effect of the application force required for the proper positioning of post 5, the parts of setting product 9 which meet the walls of canal 3 flow and consequently come to fill the empty spaces between post 5 and the inner wall of canal 3, which allows spaces of substantial volume to be filled, in particular those of ovoid shape, as shown in FIG. 2. After controlling the correct positioning of post 5, the practitioner projects light onto the outer end of the latter using a light source S, in particular a source of rays whose wavelength is in visible light, for the time that is necessary to achieve complete setting of product 9. The light rays follow transparent nucleus 7 of post 5 to light up during their passage and from within the outer sheath of photopolymerizable product 9, thereby causing the latter to set. Post 5 is thereby locked in position.

When setting product 9 is of transparent type, as specified above, the practitioner can carry out photopolymerization of the product by directly applying light to its outer surface as shown in FIG. 1, with a source of light S' placed in the proximity of the junction between post 5 and the surface of tooth 1. In this way it is possible to obtain more effective action of the light ray on setting product 9 as the pathway of the ray through the post is shorter.

Figure 3:
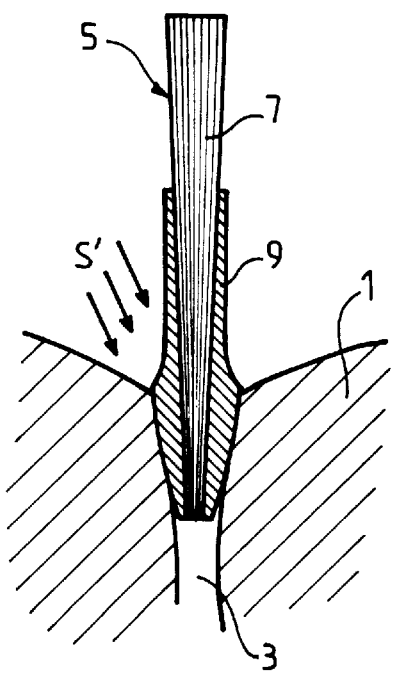
FIG. 3 is an axial, longitudinal section view of a variant of use of a reinforcement according to the invention made up of a post.

As shown in FIG. 3, it is not necessary for setting product 9 to be deposited in an equal layer over the entire periphery of central nucleus 7 of post 5. It need only be deposited on the so-called root canal part of post 5, that is to say the part intended to be placed in root canal 3. Such possibility provides extensive ease of use in respect of prehension.

The positioning of the post inside the dental cavity may also be made as described below. During a first stage, the post of the invention is positioned in the root canal as described previously, so that the parts of the setting product which come into contact with the canal walls flow under the effect of stress and perfectly line the canal contour. In a second stage, the product is caused to set, which may be partial, and the post is withdrawn from the cavity. For this purpose it is possible, before the post is positioned, to deposit in the dental cavity and/or on the post a product which facilitates the latter's removal from the "mould", such as in particular Vaseline. One therefore has in hand a post whose outer contour corresponds to that of the root canal with the exception of a few deformations due to shrinkage of the product during setting (these deformations being lesser than those produced in the prior art as mentioned above). If the setting of the product is not completed, it is possible to complete setting outside the patient's mouth, in an oven for example. It is therefore possible in accordance with the invention to harden the post thus formed only as much as is necessary for it to be withdrawn without being deformed, and the setting stage can subsequently be completed outside the patient's mouth with means known to the prior art, which allow optimal hardening of the post to be achieved. The final stage entails cementing the post in the dental cavity, in conventional manner, using a cementing product. For this purpose, this product may be placed both in the root canal and around the periphery of the post, so that the few spaces left by the slight shrinkage of the product may be easily offset.

Figure 4:
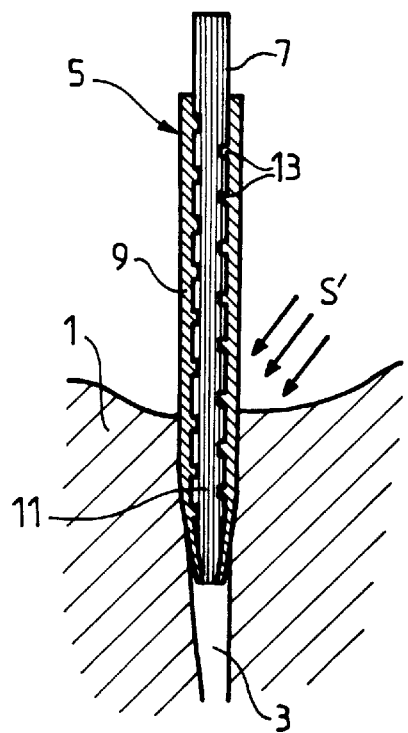
FIG. 4 is an axial, longitudinal view of another variant of use of a reinforcement according to the invention made up of a post.

In a further embodiment of the invention shown in FIG. 4, post 5 comprises a rigid nucleus 7 formed of transparent long fibres 11 which extend over its entire length. These long fibres 11 confer upon the post the rigidity required for its positioning in dental canal 3. Retainers 13 obtained in particular through machining, are made around nucleus 7 in such manner as to form small projections around the periphery of the latter to enhance the adhesion of setting product 9.

Figure 5:
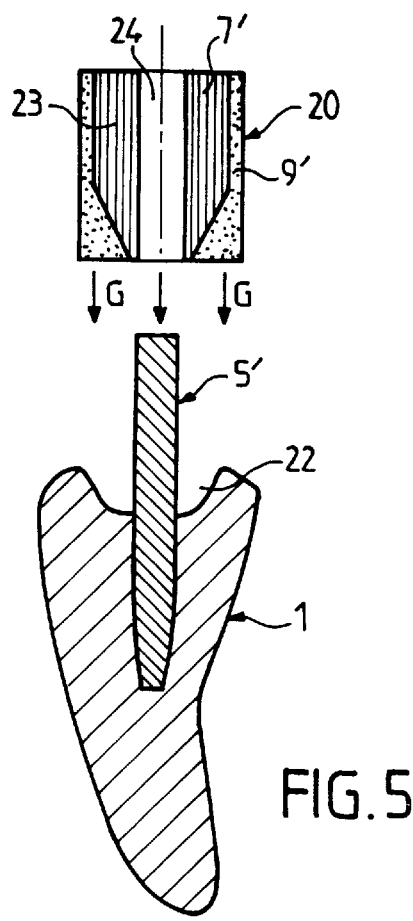
FIG. 5 is an axial, longitudinal view of a reinforcement according to the invention made up of a core before it is placed on a post bonded to a tooth.
Figure 6:
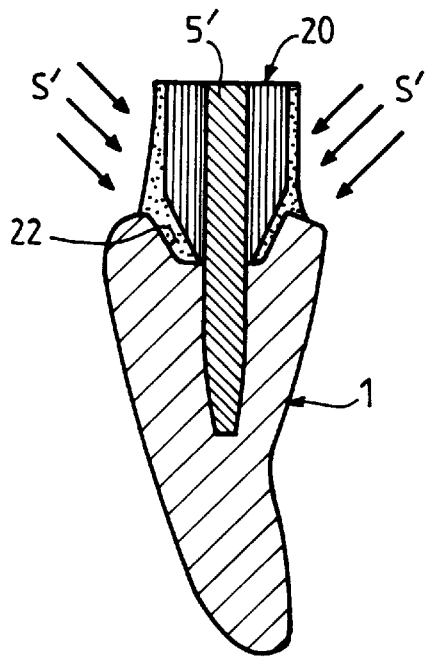
FIG. 6 is an axial, longitudinal view of a tooth fitted with a core shown in FIG. 5.

As shown in FIGS. 5 and 6, the reinforcement of the invention may also be made up of a core 20 intended to be placed on a post 5' fixed in a tooth 1. For this purpose the upper part of tooth 1 surrounding post 5 is hollowed to form a cavity 22 intended to house the base of core 20.

The latter is made up of a rigid nucleus 23 whose lower part is of truncated cone shape hollowed by an axial longitudinal canal 24, whose inner diameter corresponds to the outer diameter of post 5', in such manner that core 20 is able to be slipped over the latter. Periphery 9' of core 20 is covered by a product 9' able to flow which has the property of setting under a light ray in particular a visible or ultraviolet ray of the type used in the previous embodiment. This product extends over the entire height of core 20 so that the outer shape of the latter is of cylinder shape and its lower part comprises a greater quantity of setting product 9'.

Under these conditions the positioning on the tooth of core 20 is carried out as specified below.

Core 20 is placed over post 5' so that its axial canal 24 houses the latter, and is strongly pressed against tooth 1 with stress being exerted in the direction of arrows G so that, under this stress, product 9' flows and fills the space between the outer walls of cavity 22 and the walls of core 20. As described previously, light is applied to product 9' using a light ray, in particular a visible or possibly an ultraviolet ray, so as to cause the product to set. With this particularly easy, quick method the core can be cemented to the tooth in a manner in which all the free spaces existing between the tooth and the core are filled with a product that has set, so that the core is held in particularly effective manner onto post 5' and tooth 1.

Figure 7:
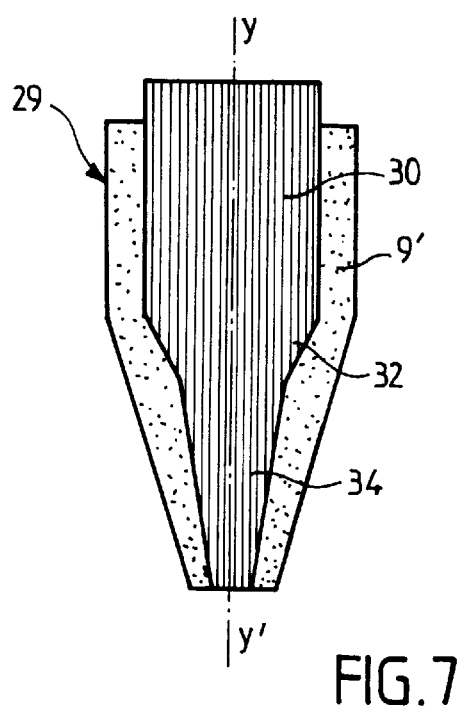
FIG. 7 is an axial, longitudinal view of a variant of use of a reinforcement according to the invention which forms both a post and a core before it is placed in a tooth.
Figure 8:
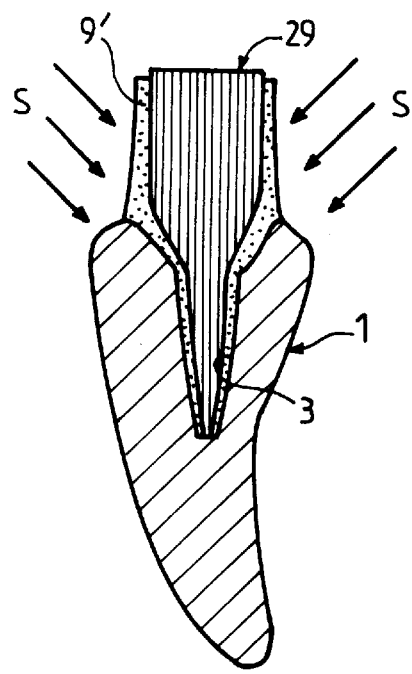
FIG. 8 is an axial, longitudinal view of a reinforcement shown in FIG. 7 after it has been placed in the tooth.

In a variant of embodiment shown in FIGS. 7 and 8, a reinforcement 29 of the invention is made up both of a post bonded in the tooth and of a core. Therefore in FIG. 7, reinforcement 29 is made up of a central nucleus comprising a upper cylindrical part 30 followed by a part of truncated cone shape 32 which is extended downwards by a second part of truncated cone shape 34 that has a smaller angle of slant than part 32 in relation to longitudinal axis yy' of reinforcement 29. The periphery of the latter is covered by a setting product 9' having the properties previously described in the two examples given above. Under these conditions the positioning of reinforcement 29 is carried out as described below.

After clearing root canal 3 of tooth 1, reinforcement 29 is pressed into canal 3 so that under the force applied, setting product 9' flows and fills the cavities between dental canal 3, floor 22 of tooth 1 and the central part of reinforcement 29. As previously, after this placing in position, light is applied to setting product 9' using a source of visible light S to cause it to set thereby fixing reinforcement 29 in tooth 1.

According to the invention, the setting product may also be a product which self-polymerises under the action of means other than a light ray. The product may for example by set under the effect of a rise in temperature, in particular to a temperature above normal human body temperature. The extent of setting obtained may be full or partial as described previously.

In one embodiment of use of the invention, the means of longitudinal rigidity are made up of the setting product whose central part is provided for this purpose, and over its entire length, with long fibres that are embedded in it.

In another embodiment of use of the invention, the means of longitudinal rigidity comprise optic fibres in the central axis.

Also, the setting product may contain fibres which, like the loads, can allow control over flow qualities. These fibres may be short fibres, in particular positioned at random, or long fibres positioned longitudinally or wound around the rigid nucleus of the reinforcement.

What is claimed is:

1. Dental reinforcement intended to be placed in a dental cavity comprising:

longitudinally extending stiffening means, having a part intended to be fixed in said cavity, for providing rigidity to said cavity;

said part having a periphery which comprises thereon a photopolymerizable setting product structured and arranged:

(a) to flow in a first dental cavity insertion mode under the effect of stress, in such a manner as to follow the contour of the walls of the cavity in which the dental reinforcement is positioned;

(b) to set in a second mode after placed in said cavity and subjected to light rays; and (c) to adhere to said periphery and to be removable from said cavity with said stiffening means in a third mode.

2. The dental reinforcement according to claim 1, wherein the dental reinforcement is in the form of a dental post which comprises the longitudinally extending stiffening means.

3. The dental reinforcement according to claim 1, wherein the dental reinforcement comprises a dental core for placement on the longitudinal extending stiffening means, said dental core having an axial longitudinal canal for accommodating the longitudinally extending stiffening means therethrough.

4. The dental reinforcement according to claim 1, wherein the dental reinforcement comprises an anterior part forming a post, intended to be placed in a root canal of a tooth, and a posterior part forming a dental core.

5. The dental reinforcement according to claim 1, wherein the stiffening means comprise a nucleus formed by transparent long glass or quartz fibers embedded in a synthetic resin.

6. The dental reinforcement according to claim 5, wherein the stiffening means comprise optic fibers.

7. The dental reinforcement according to claim 1, wherein the setting product contains pyrogenated or colloidal silica.

8. The dental reinforcement according to claim 7, wherein the setting product further contains short fibers.

9. The dental reinforcement according to claim 7, wherein the setting product further contains long fibers.

10. The dental reinforcement according to claim 9, wherein the long fibers are wound around the stiffening means.

11. Method of placing a dental reinforcement in a dental cavity which comprises the following stages:

providing a longitudinal rigid element having a periphery;

covering at least the periphery of the longitudinal rigid element with a photopolymerizable setting product able to flow under the action of a stress to obtain a dental reinforcement;

placing said reinforcement inside the cavity so as to cause said product to flow under the effect of stress resulting from the positioning of the reinforcement in the cavity, said product following the contour of the walls of the cavity in which the dental reinforcement is positioned;

subjecting said photopolymerizable product to light rays in order to set, at least in part;

withdrawing said reinforcement from the cavity;

placing a cementing product in at least one of said cavity and on the periphery of said reinforcement; and replacing the reinforcement in the cavity so that it may be cemented into place.

* * * * *